United States Patent [19]

Kuriyama

[11] Patent Number: 4,835,452
[45] Date of Patent: May 30, 1989

[54] LIQUIDPROOF BATTERY-POWERED APPLIANCE

[75] Inventor: Shunichi Kuriyama, Hyogo, Japan
[73] Assignee: Sanyo Electric Co., Ltd., Japan
[21] Appl. No.: 98,013
[22] Filed: Sep. 17, 1987
[30] Foreign Application Priority Data
Sep. 19, 1986 [JP] Japan ................. 61-222584
[51] Int. Cl.⁴ .............................. H02J 7/00
[52] U.S. Cl. ............................ 320/2; 320/46
[58] Field of Search ......................... 320/2, 46
[56] References Cited

U.S. PATENT DOCUMENTS

| | | | |
|---|---|---|---|
| 4,213,078 | 7/1980 | Ferrell et al. | 320/2 |
| 4,363,169 | 12/1982 | Nasu et al. | 30/41 |
| 4,451,980 | 6/1984 | Shirakawa et al. | 320/46 |

FOREIGN PATENT DOCUMENTS

| | | |
|---|---|---|
| 47-39542 | 11/1972 | Japan . |
| 58-5329 | 1/1983 | Japan . |
| 60-24882 | 2/1985 | Japan . |
| 61-79457 | 5/1986 | Japan . |
| 991165 | 5/1965 | United Kingdom . |
| 1513499 | 6/1978 | United Kingdom . |
| 2115973A | 9/1983 | United Kingdom . |

Primary Examiner—Peter S. Wong
Assistant Examiner—Anita M. Ault
Attorney, Agent, or Firm—Darby & Darby

[57] ABSTRACT

In a liquidproof battery-powered appliance, a battery insertion opening formed in the bottom of a battery accommodation casing accommodating a rechargeable battery and provided with parts including a motor and a printed circuit board is closed liquidtight by a cover member provided with a gas vent valve, and, after insertion of the battery accommodation casing into a body casing through a bottom opening of the body casing, the bottom opening is closed liquidtight by a flange formed at a peripheral edge of the battery insertion opening of the battery accommodation casing. By the above arrangement, the casings can be simply and reliably sealed liquidtight, and gas that may be generated in a very large amount from the battery in an unusual operating condition can be safely and reliably exhausted to the outside of the appliance.

2 Claims, 3 Drawing Sheets

LIQUIDPROOF BATTERY-POWERED APPLIANCE

BACKGROUND OF THE INVENTION

1. Field of the Invention

This invention relates to a small-sized liquidproof battery-powered appliance such as a waterproof electric shaver or an electric toothbrush driven by a miniature motor whose power source is a rechargeable secondary battery incorporated in the appliance. More particularly, this invention relates to a liquidtight structure of such an appliance and relates also to a gas venting structure of the appliance for venting gas generated from the secondary battery to the outside of the appliance.

2. Description of the Prior Art

It is commonly known that, in a liquidproof battery-powered appliance having a secondary battery incorporated in its liquidtight body casing, hydrogen gas is generated from the secondary battery during discharging and recharging the secondary battery, as described in Japanese Utility Model Publication No. 47-39542 (1972) or Japanese Utility Model Publication No. 58-5329 (1983). The hydrogen gas may be generated in a very large amount due to an unusual operating condition such as an overcharge or an overdischarge and may be jetted from a battery safety valve to fill the internal space of the body casing of the appliance. In such a case, it is necessary to immediately exhaust the hydrogen gas to the outside of the appliance.

A gas venting structure for exhausting hydrogen gas to the outside of a liquidproof battery-powered appliance such as a waterproof electric shaver is known. As a prior art example of such a structure, Japanese Patent earlier publication No. 60-24882 discloses a structure for exhausting hydrogen gas generated from a storage battery in an electric shaver and accumulating in a body casing of the electric shaver.

According to the disclosure of Japanese Patent earlier publication No. 60-24882 cited above, a positive terminal pin of the storage battery is shaped in the form of a small pipe and is locally spot-welded at its flanged base end portion to the positive electrode of the storage battery, and the flanged portion of the positive terminal pin is covered with a battery packing of rubber material covering the position electrode of the storage battery. Gas generated in the storage battery is exhausted from a gas vent hole provided in the positive electrode and accumulates in a gas reservoir formed inside the battery packing. The gas accumulating in the gas reservoir flows through a gap formed between the packing and the positive electrode into the positive terminal pin to be exhausted to the outside of the housing of the electric shaver.

A gas venting structure using such a hollow electrode terminal pin to vent gas generated inside an appliance to the outside of the appliance is also described in U.S. Pat. No. 4,451,980.

However, a prior art gas venting structure as described above has had the problem of an inevitable increase in the number of assembling steps since it includes many small parts including a packing covering the positive electrode of a storage battery and a hollow electrode terminal pin for venting gas. Also, the prior art gas venting structure has not been fully satisfactory from the aspects of securing the quality of connection parts and the tightness of seals.

Japanese Utility Model earlier publication No. 61-79457 discloses a liquidproof battery-powered appliance in which a battery unit constituted by the combination of a plurality of secondary batteries, a battery cap mounted on the upper part of these secondary batteries to prevent relative displacement of these secondary batteries, a rubber packing intimately covering the lower part of the secondary batteries and a packing casing fitting over the rubber packing is encased in a battery accommodation casing, and the battery unit encased in the battery accommodation casing is disposed inside a body casing of the appliance.

However, the disclosed appliance has also had the problem of an inevitable increase in the number of assembling steps resulting from an increased number of parts. Further, the disclosed appliance has required liquidtight seals at an increased number of locations.

On the other hand, a liquidtight structure for a battery-powered appliance of this kind is disclosed in, for example, U.S. Pat. No. 4,363,169. However, the liquidtight structure described in this U.S. patent requires various parts of complex shapes including an inner cover, a lifting cam member, an outer cover, a pawl and a dial in order to carry out both the function of mechanically holding the battery in position and the function of liquidtight sealing the battery insertion opening. Therefore, the proposed liquidtight structure has had the problem of a high manufacturing cost. Also, the proposed liquidtight structure has not been satisfactory in that venting of gas is not taken into consideration.

SUMMARY OF THE INVENTION

It is an object of the present invention to solve the prior art problems described above and to provide a liquidproof battery-powered appliance in which its outer casing can be sealed liquidtight by a small number of parts.

Another object of the present invention is to provide a battery-powered appliance of the type described above which ensures reliable gas venting together with the liquidtight sealing of its outer casing.

In accordance with the present invention, there is provided a liquidproof battery-powered appliance comprising a generally hollow cylindrical outer casing having a bottom opening, an inner casing holding parts including a motor and a printed circuit board thereon and having a battery accommodation space for accommodating a rechargeable battery therein in liquidtight relation, and means provided on the bottom of the inner casing for closing the bottom opening of the outer casing in liquidtight relation.

Because of the above construction, the inner casing of the appliance can be reliably and simply sealed liquidtight by a small number of parts required for the liquidtight sealing, and the costs required for assembling can be decreased.

It is preferable that the means provided on the bottom of the inner casing includes a battery insertion opening communicating with the battery accommodation space and a cover member closing liquidtight the battery insertion opening.

It is also preferable that gas venting means including a gas vent valve is associated with the cover member.

Because of the provision of the liquidtight structure on the bottom of the inner casing together with such gas venting means, the outer casing of the appliance can be protected liquidtight against intrusion of a liquid, and gas that may be generated in a very large amount in the battery accommodation space due to an overcharge or an overdischarge of the battery can be reliably exhausted to the outside of the appliance thereby securing the safety of the appliance.

It is also preferably that the battery insertion opening of the inner casing is formed at its peripheral edge with a flange closing liquidtight the bottom opening of the outer casing. By the provision of the flange, the bottom opening of the outer casing can be simply and reliably closed liquidtight.

It is further preferable that the flange is formed with a recess, and a pair of charging current feeding pins are erected in this recess without being exposed from the recess. Because of the above arrangement, the secondary battery enclosed in the battery accommodation space can be simply charged from an external source of charging current.

DETAILED DESCRIPTION OF THE PREFERRED EMBODIMENT

An embodiment of the liquidproof battery-powered appliance of the present invention, when applied to a reciprocating type electric shaver, will now be described in detail with reference to FIGS. 1 to 3 of the drawings.

Figure 2:
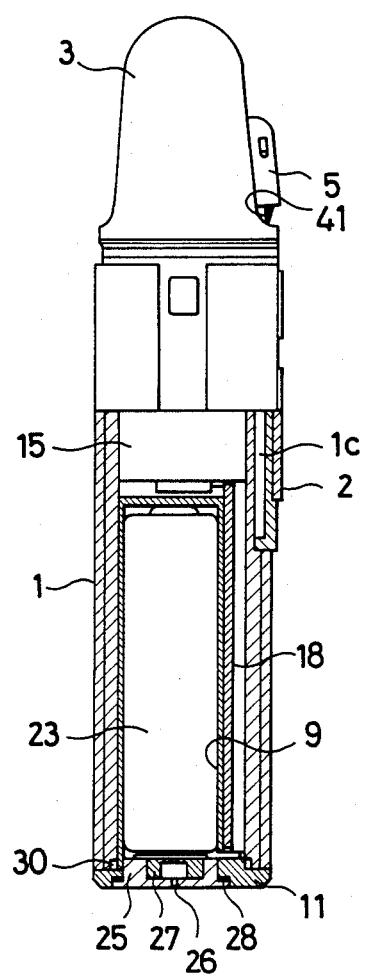
FIG. 2 is a partly sectional, side elevation view of the electric shaver, the section being taken along the line II—II' in FIG. 1.
Figure 3:
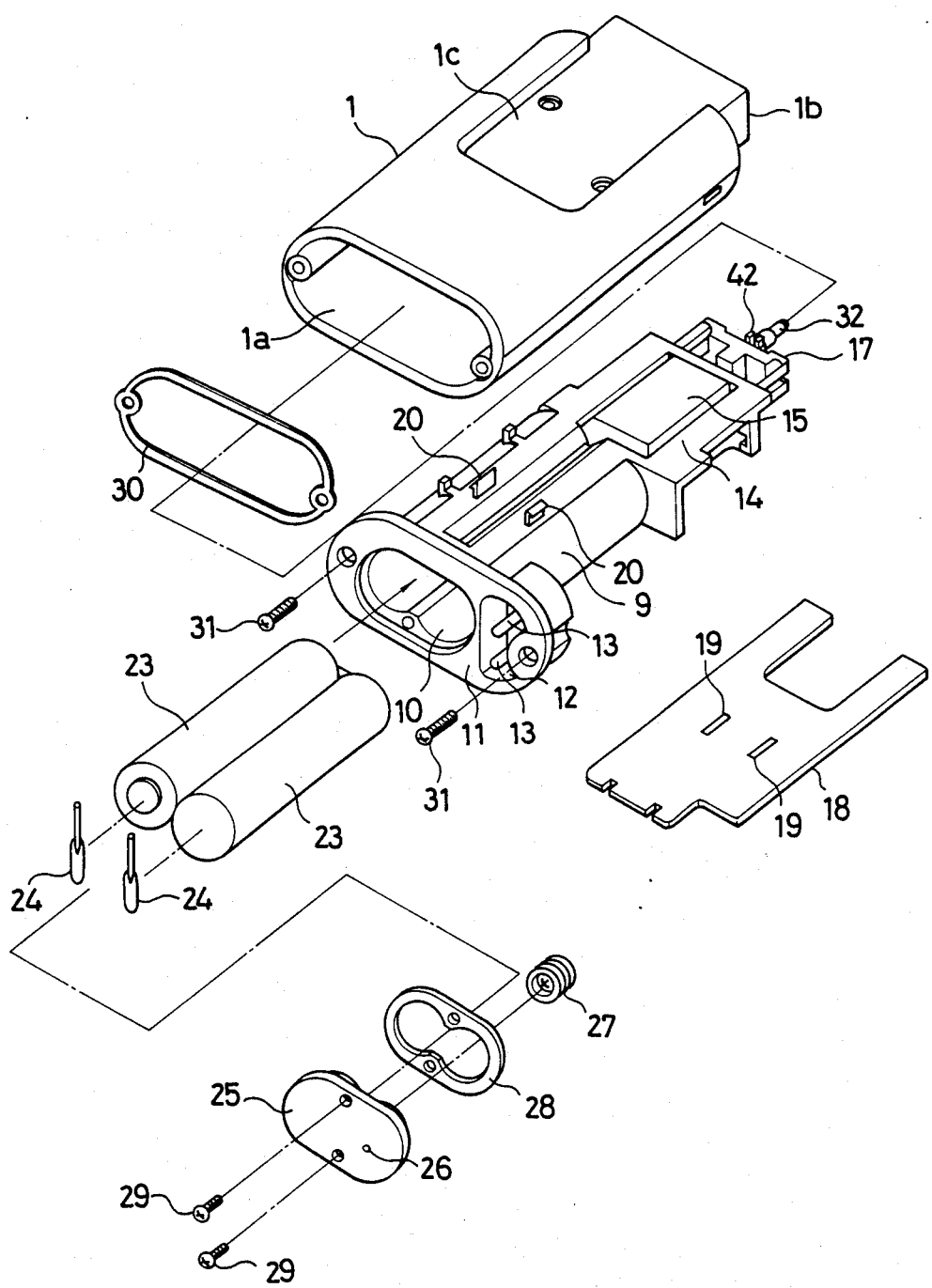
FIG. 3 is an exploded perspective view of principal parts of the electric shaver.

As best shown in FIG. 3, a generally hollow cylindrical body casing 1 providing the external configuration of the electric shaver has an opening 1a at its bottom, a projection 1b at its upper part and a recess 1c at its rear part. This recess 1c is contiguous to the projection 1b. As shown in FIG. 2, an actuating member 2 for actuating a trimmer unit described later is slidably mounted in the recess 1c.

An outer blade frame 3 made of an aluminum die casting is detachably mounted on the top of the body casing 1 in such a relation as to conceal the projection 1b of the body casing 1. The outer blade frame 3 has a top opening in which an outer blade member 4 electrically casted with nickel having many beard guiding perforations is detachably secured.

At an upper part of the trimmer actuating member 2, a trimmer unit 5 is mounted so as to be swingable around a pivot, that is, so as to be actuatable between its horizontally projecting operative position and its vertically collapsed inoperative position. The trimmer unit 5 includes a stationary comb-shaped blade member fixed to a base made of a synthetic resin and movable comb-shaped blade member 41 slideable along the stationary comb-shaped blade member. When the actuating member 2 is moved upward in FIG. 2, the trimmer unit 5 takes its horizontally projecting operative position while moving upward or standing up by swinging at the position, while when the actuating member 2 is moved downward in FIG. 2, the trimmer unit 5 takes its vertically collapsed inoperative position while moving downward or being collapsed at that position.

Figure 1:
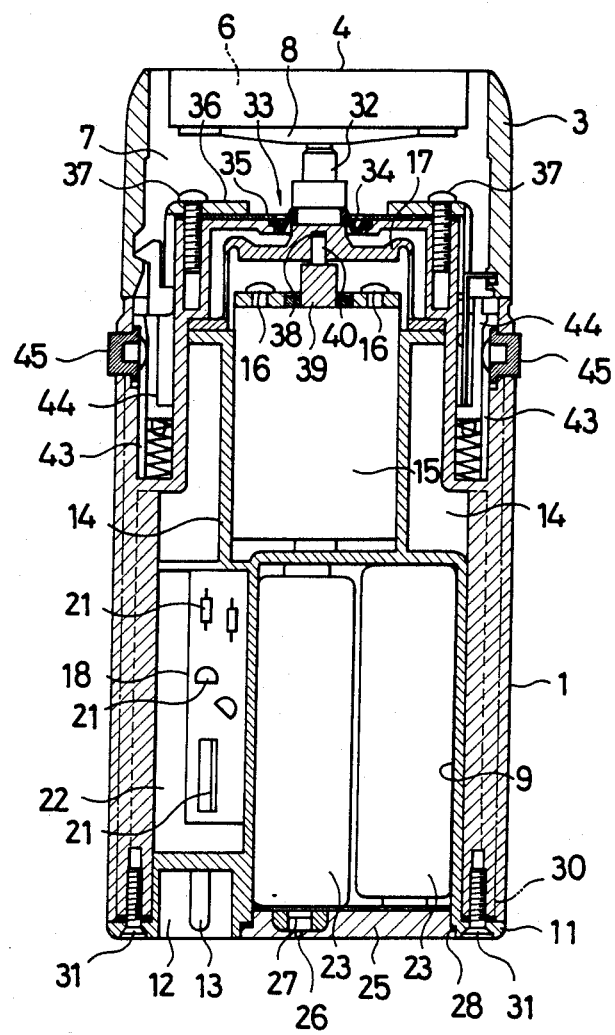
FIG. 1 is a sectional, front elevation view of a reciprocating type electric shaver which is an embodiment of the liquidproof battery-powered appliance according to the present invention.

As shown in FIG. 1, a shavings receiving space 7 is defined between the outer blade frame 3 and the upper part of the body casing 1, and an inner blade member 6 is disposed in this space 7. This inner blade member 6 includes a base made of a synthetic resin and many small semicircular inner blades (not shown) planted in the base by insert molding and is detachably mounted on an inner blade supporting member 8 made of a synthetic resin. In the shaving operation, the small inner blades slide along the inner surface of the outer blade member 4 so that beards taken into the shavings receiving space 7 through the beard guiding perforations of the outer blade member 4 can be cut.

A battery accommodation casing 9 is inserted through the bottom opening 1a of the body casing 1 to be encased within the body casing 1. A battery insertion opening 10 is provided in the bottom of the battery accommodation casing 9. A flange 11 is formed at the peripheral edge of the battery insertion opening 10. A recess 12 is formed at one end of the flange 11, and a pair of charging current feeding pins 13 are erected in the recess 12 without being exposed from the recess 12 so as to feed a charging current to secondary batteries 23 described later.

On the other hand, a motor holding frame 14 is formed integrally as an upper extension of the battery accommodation casing 9, and a motor 15 is fixed in the motor holding frame 14 by screws 16. An oscillator 17 is fixed at the lower ends of its legs to the upper end of the motor holding frame 14 by means such as engaging fingers. A printed circuit board 18 is mounted on the rear wall of the battery accommodation casing 9. A pair of lugs 20 projecting from this rear wall of the battery accommodation casing 9 are inserted into and engaged by a corresponding pair of slots 19 formed in the printed circuit board 18, so that the printed circuit board 18 is fixed to both the battery accommodation casing 9 and the motor holding frame 14.

Electrical parts 21 constituting a battery charge-discharge circuit and a motor driver circuit are mounted on the printed circuit board 18 in a relation concentrated in a cavity 22 formed on one side of the battery accommodation casing 9.

A plurality of, for example, two rechargeable secondary batteries 23 are inserted through the battery insertion opening 10 into the battery accommodation casing 9 to be stored in this casing 9. Lead strips 24 spot-welded to the respective secondary batteries 23 are led out from a small hole bored in one of the side walls of the battery accommodation casing 9 to be soldered to the printed circuit board 18. This small hole is then plugged by an epoxy resin so that intrusion of water and leakage of gas through this portion can be prevented.

A cover member 25 closes the battery insertion opening 10 of the battery accommodation casing 9 after insertion of the secondary batteries 23. This cover member 25 is formed with a small gas vent hole 26. Further, a gas vent valve 27 is mounted opposite the gas vent hole 26. The cover member 25 is fixed to the flange 11, formed on the peripheral edge of the battery insertion opening 10, through a packing 28 by screws 29. This arrangement seals liquidtight the interior of the battery accommodation casing 9.

Such a unit having the secondary batteries 23 accommodated therein and having the motor 15, oscillator 17 and printed circuit board 18 integrally mounted thereon is inserted into the body casing 1 through the bottom opening 1a of the body casing 1. The flange 11 formed integrally with the battery accommodation casing 9 is brought into abutment through a packing 30 with the peripheral edge of the bottom opening 1a of the body casing 1 and is fixed thereto be screws 31, thereby simply and reliably completing a liquidtight seal for the body casing 1.

When the electric shaver is thus assembled, an oscillation shaft 32 extending from the oscillator 17 protrudes upward through a hole 33 bored in the upper end of the body casing 1. This area is sealed liquidtight by a bead-like sealing member 34 peripheral edge of which is fixed on inner peripheral edge of the hole 33 by screws 37 screwed into a holding plate 35 and a trimmer unit mounting member 36.

The oscillator 17 if formed at its lower central part with a cam bore 38 which loosely receives therein a pin 40 erected at an eccentric position on the outer surface of the upper end of a rotary shaft 39 of the motor 15. Therefore, when the motor 15 rotates, the pin 40 on the rotary shaft 39 makes circular motion which causes single harmonic oscillation of the oscillator 17. This single harmonic motion of the oscillator 17 is transmitted through the oscillation shaft 32 to the inner blade supporting member 8, and the inner blade member 6 consisting of the aforementioned many semicircular small inner blades reciprocates along the inner surface of the outer blade member 4 while making sliding contact therewith. Thus, beards taken into the shavings receiving space 7 through the beard guiding perforations of the outer blade member 4 are cut by the cooperation of the inner and outer blade members 6 and 4.

Further, as shown in FIGS. 2 and 3, the oscillation shaft 32 of the oscillator 17 is provided with a trimmer drive-force transmitting part 42 which transmits drive force to the comb-shaped movable blade member 41 in the horizontally projecting operative position of the trimmer unit 5.

Further, as shown in FIG. 1, the body casing 1 is formed with a pair of vertical recesses 43 in an upper part of its both side walls respectively, and a locking mechanism 44 and an actuating button 45 are disposed in each of these recesses 43 for locking and unlocking the detachable outer blade frame 3.

When, the electric shaver having the construction described above, hydrogen gas fills the internal space of the battery accommodation casing 9 as a result of repeated charging and discharging of the secondary batteries 23, the gas vent valve 27 is forcedly opened by the pressure of the hydrogen gas, and any excess of the hydrogen gas is exhausted through the small hole 26 to the outside of the battery accommodation casing 9. Thus, the battery accommodation casing 9 is protected against destruction due to accidental explosion occurring when the amount of hydrogen gas increases to such a dangerous value that the mixture ratio between the hydrogen gas and the oxygen in the atmospheric air exceeds a predetermined critical limit.

In the appliance according to the present invention, the battery insertion opening 10 provided in the bottom of the battery accommodation casing 9 is closed liquidtight by the cover member 25 having the gas vent valve 27, and, when the battery accommodation casing 9 is inserted into the body casing 1 through the bottom opening 1a of the body casing 1, the bottom opening 1a is closed liquidtight by the flange 11 formed on the peripheral edge of the battery insertion opening 10 of the battery accommodation casing 9. Thus, the battery accommodation casing 9 and the body casing 1 can be sealed liquidtight by the liquidtight sealing arrangement of simple structure, so that the assemblage of the appliance can be facilitated or improved, and hydrogen gas generated during charging and discharging can be reliably exhausted to the outside of the appliance. Further, there is utterly no possibility of internal intrusion of gas into the body casing 1 as well as external intrusion of water or moisture into the body casing 1. Thus, a liquidproof electric shaver having very high reliability can be provided.

I claim:

1. A liquidproof battery-powered appliance comprising a generally hollow cylindrical outer casing having a bottom opening, and an inner casing holding parts including a motor and a printed circuit board thereon, and having a battery accommodation space for accommodating a rechargeable battery therein in liquid-tight relation, said inner casing having means for closing the bottom opening of said outer casing in liquidtight relation, said inner casing including a battery insertion opening communicating with said battery accommodation space and a cover member closing liquid-tight said battery insertion opening, said cover including gas venting means including a gas vent valve associated therewith, said battery insertion opening of said inner casing formed at its peripheral edge with a flange closing liquid-tight said bottom opening of said outer casing.

2. A liquidproof battery-powered appliance according to claim 1, wherein said flange is formed with a recess, and a pair of charging current feeding pins are erected in said recess without being exposed from said recess.

* * * * *